United States Patent [19]

Coke

[11] Patent Number: 5,712,164
[45] Date of Patent: Jan. 27, 1998

[54] METHOD FOR REDUCING CONTAMINATION OF IN VITRO CULTURES OF SHOOT MATERIAL

[75] Inventor: Jay Eric Coke, Summerville, S.C.

[73] Assignee: Westvaco Corporation, New York, N.Y.

[21] Appl. No.: 456,757

[22] Filed: Jun. 1, 1995

Related U.S. Application Data

[63] Continuation-in-part of Ser. No. 258,719, Jun. 13, 1994, abandoned.

[51] Int. Cl.$^6$ ........................................................ C12N 5/00
[52] U.S. Cl. ............................ 435/420; 435/431; 47/6; 47/7
[58] Field of Search .......................... 435/240.45, 240.1, 435/240.3, 240.54, 240.49, 420, 431; 47/6, 7; 800/200

[56] References Cited

U.S. PATENT DOCUMENTS

| | | | |
|---|---|---|---|
| 4,052,817 | 10/1977 | Seibert | 435/430 |
| 5,099,600 | 3/1992 | Crawford et al. | 47/6 |
| 5,244,802 | 9/1993 | Rangan | 435/427 |
| 5,304,725 | 4/1994 | Nelson | 800/200 |

OTHER PUBLICATIONS

Reed, B. J. Amer. Soc. Hort. Sci vol. 118(6), pp. 890–895, 1993.

Aitken–Christie, J., and M. Connett. Micropropagation of forest trees. In Transplant Production Systems. K. Kurata and T. Kozai (eds). *Kluwer Academic Publishers*, The Netherlands, 1992.

Berthon, J. –Y., N. Boyer, and T. Gaspar. Uptake, distribution and metabolism of 2,4–dichlorophenoxyacetic acid in shoots of juvenile and mature clones of *Sequoiadendron giganteum* in relation to rooting in vitro. *Plant Physiology and Biochemistry* 29:355–362, 1991.

da Câmara Machado, M.L., A. da Câmara Machado, V. Hanzer B. Kalthoff, H. Weiss, D. Mattanovich, F. Regner, and H. Katinger, 1991. A new, efficient method using 8–hydroxy–quinolinol–sulfate for the initiation and establishment of tissue cultures of apple from adult material. *Plant Cell, Tissue and Organ Culture* 27:155–160, 1991.

Duhem, K., N. Le Mercier, and Ph. Boxus. Difficulties in the establishment of axenic in vitro cultures of field collected coffee and cacao germplasm. *Acta Horticulturae* 225:67–75, 1988.

Debergh, P. C., and L. J. Maene. A scheme for commercial propagation of ornamental plants by tissue culture. *Scientia Horticulturae* 14:335–345, 1981.

Enjalric, F., M.P. Carron, and L. Lardet. Contamination of primary cultures in in tropical areas: The case of *Hevea Brasiliensis*. *Acta Horticulturae* 225:57–65, 1988.

Hammerschlag, F.A., R.R. Bauchan, and R. Scorza. Factors influencing in vitro multiplication and rooting of peach cultivars. *Plant Cell, Tissue and Organ Culture* 8:235–242, 1987.

Jones, O. P., and W. C. C. Hadlow. Juvenile–like character of apple trees produced by grafting scions and rootstocks produced by micropropagation. *Journal of Horticultural Science* 64:395–401, 1989.

Jones, O. P., C.A. Pontikis, and M. E. Hopgood. Propagation in vitro of five apple scion cultivars. *Journal of Horticulture Science* 54:155–158, 1979.

Leifert, C., and W. M. Waites. Contaminants of plant tissue cultures. *International Association of Plant Tissue Culture Newsletter* 60:2–13, 1990.

Mac An tSaoir, S. and M. Kabrianis. Establishment of explants from 200–year–old *Quercus petraea* in culture. *Ann Sci For* 50, Suppl. 1: 336s–339s, 1993.

Marks, T. R. Micropropagation of hardy ornamental nursery stock. In Micropagation in Horticulture: Practice and Commercial Problems.

Monteuuis, O. In vitro meristem culture of juvenile and mature *Sequoiadendron giganteum*. *Tree Physiology* 3:265–272, 1987.

Oliphant, J. L. Consideration of juvenility and maturity in the micropropagation of the *Metrosideros* species. *Acta Horticulturae* 227:482–484, 1988.

Pliego–Alfaro, F., and T. Murashige. Possible rejuvenation of adult avocado by graftage onto juvenile rootstocks in vitro. *HortScience* 22:1321–1324, 1987.

Polito, V. S., and V. Alliata. Growth of calluses derived from shoot apical meristems of adult and juvenile English ivy (*Hedera helix* L.). *Plant Science Letters* 22:387–393, 1981.

Poulsen, G. B. Elimination of contaminating micro–organisms from meristem culture of apple rootstock M26. *Acta Horiculturae* 225:193–197, 1988.

Preece, J. E., C. A. Huetteman, W. C. Ashby, and P. L. Roth. Micro–and cutting propagation of silver maple. I. Results with adult and juvenile propagules. *Journal of the American Society of Horticultural Science* 116:142–148, 1991.

Robbins W. J., and A. Hervey. Tissue culture of callus from seedling and adult stages of *Hedera helix*. *American Journal of Botany* 57:452–457, 1970.

Sánchez, M. C., and A. M. Vieitez. In vitro morphogenic competence of basal sprouts and crown branches of mature chestnut. *Tree Physiology* 8:59–70, 1991.

Struve, D. K., and R. D. Lineberger. Restoration of high adventitious root regeneration potential in mature *Betula papyrifera* Marsh. softwood stem cuttings. *Canadian Journal of Forest Research* 18:265–269, 1988.

Sudarsono and R. G. Goldy. Growth regulator and axillary bud position effects on in vitro establishment of *Vitis rotundifolia*. *HortScience* 26:304–307, 1991.

Warrag, E. I, M. S. Lesney, and D. L. Rockwood. Micropropagation of field tested superior *Eucalyptus grandis* hybrids. *New Forests* 4:67–79, 1990.

Primary Examiner—Leon B. Lankford, Jr.
Assistant Examiner—Christopher R. Tate
Attorney, Agent, or Firm—Daniel B. Reece, IV; Terry B. McDaniel; Richard L. Schmalz

[57] ABSTRACT

This invention relates to a method for reducing contamination of in vitro cultures. In particular, this invention relates to a method for reducing contamination of in vitro cultures of woody plant mature shoot material and shoot material of outdoor origin.

10 Claims, No Drawings

METHOD FOR REDUCING CONTAMINATION OF IN VITRO CULTURES OF SHOOT MATERIAL

This application is a continuation-in-part of my commonly assigned, U.S. patent application Ser. No. 08/258,719 filed Jun. 13, 1994, now abandoned, entitled "Method For Reducing Contamination Of In Vitro Cultures Of Shoot Material."

FIELD OF INVENTION

This invention relates to a method for reducing contamination of in vitro cultures. In particular, this invention relates to a method for reducing contamination of in vitro cultures of woody plant mature shoot material and shoot material of outdoor origin.

BACKGROUND OF THE INVENTION

For many woody plants, tissue culture techniques offer an effective means for rejuvenating and propagating superior, tested individuals. However, with many species of plants contamination is often a major problem with tissue cultures of mature shoot material (Aitken-Christie and Connett 1992). Elimination of contamination in plant tissue cultures is commonly accomplished by surface-sterilization of the explant and the use of aseptic technique in subsequent procedures. However, in studies using surface-sterilization techniques that were effective for seedling material, mature shoots have exhibited higher contamination frequencies than their seedling counterparts. This is due in part to the difference in the external anatomy of juvenile and mature shoots (Warrag et al. 1990). For example, in the genus Pinus young seedlings have relatively long primary needles which extend away from the stem, and rarely have needle fascicles. This open anatomy makes surface-sterilization efficient since most surface bacteria and fungi are exposed to the sterilization agents. In contrast, fully developed mature shoots have short, appressed, scale-like primary needles and abundant needle fascicles. These structures provide many sites for fungi and bacteria to escape the effect of surface-sterilization treatments.

In addition to anatomical differences in juvenile and mature shoots, the environment under which the donor plants are grown can influence microbial populations which, in turn, can influence subsequent in vitro contamination (Enjalric et al. 1988). Seedling shoots can easily be grown in a relatively clean greenhouse or growth chamber. In contrast, mature shoots (especially those from large trees) often originate from plants grown under field conditions. As a result mature shoot explants usually begin with a higher number of surface contaminants (i.e., fungi, bacteria, and yeast) than seedling explants; and this higher frequency of microbes tends to reduce the success of initial surface-sterilization treatments (Leifert and Waites 1990).

Thus, researchers were confronted with the problem of increased in vitro contamination associated with the use of mature shoot material and with material of outdoor origin, a problem which traditional surface-sterilization techniques failed to solve. In attempts to resolve this problem researchers have employed several methods to ensure initially cleaner explant material. For example, many investigators working with shoot material from various species have grown plants in greenhouses or growth chambers (Robbins and Hervey 1970, Polito and Alliata 1981, Hammerschlag et al. 1987, Oliphant 1988, Berthon et al. 1991, Preece et al. 1991, Sanchez and Vieitez 1991, Sudarsono and Goldy 1991) and have avoided overhead watering (Debergh and Maene 1981, Marks 1986) prior to in vitro culturing as a means of minimizing bud and shoot infestation by bacteria and fungi.

The transfer of plants to a greenhouse environment has often required that cuttings from the donor plant be rooted and planted in pots. Difficult-to-root mature shoot material from large, field-grown trees must be grafted onto seedling rootstocks in order to be grown under greenhouse or growth chamber conditions prior to being cultured (Monteuuis 1987, Pliego-Alfaro and Murashige 1987, Struve and Lineberger 1988, Jones and Hadlow 1989). Grafted plants must often be grown for extended periods of time in order to regain the size necessary to supply adequate explant material. This grafting requirement also increases the opportunity to encounter problems associated with long-term graft incompatibility. Studies with grafted mature *Pinus taeda* L. hedges demonstrated that the use of a greenhouse environment in midsummer to isolate shoots was effective in reducing bacterial contamination, but was ineffective in reducing fungal contamination. This difference in contamination is presumably a result of the means by which each of these contaminants travels. Bacteria usually require the assistance of a vector in order to travel from one place to another. Examples of such vectors include splashing water, dust, pollen, insects, and birds. As the greenhouse environment was adequate in controlling these vectors, the transport of bacteria to the shoots were reduced. Fungi, on the other hand, travel readily with air currents. Thus contaminating fungi easily moved into and throughout the greenhouse during the summer months when fans and vents were in operation for cooling.

In another attempt to obtain initially cleaner explant material, some researchers have tried the pre-culture application of anti-microbial substances to donor plants as a way to reduce the number of viable contaminants on shoots, thereby increasing the efficiency of surface-sterilization (Jones et al. 1979, Duhem et al. 1988, Enjalric et al. 1988, Oliphant 1988, da Camara Machado et al. 1991). Antibiotics, fungicides, and ethanol have all been used as antimicrobial agents for preculture treatments. In an earlier study with mature *Pinus taeda* shoots, pre-culture foliar applications of fungicides (CAPTAN and BENLATE) during shoot development reduced subsequent in vitro fungal contaminations, but had little effect on the incidence of bacterial contaminations. (CAPTAN is a fungicide commercially available from ICI Americas Inc., Wilmington, Del. BENLATE is a fungicide commercially available from IE Dupont de Nemours and Company, Inc., Wilmington, Del.)

Several investigators have incorporated antimicrobial agents in the nutrient medium as a means to eliminate contamination in shoot cultures. This approach has met with limited success. In several examples the growth of contaminants on the nutrient medium was slowed, but the elimination of contaminants on the explant itself was negligible (Duhem et al. 1988, Enjalric et al. 1988). In some cases the incorporation of antibiotics in the nutrient medium resulted in phytotoxic effects on the explant (Debergh and Maene 1981, Duhem et al. 1988, Enjalric et al. 1988, Poulsen 1988).

Therefore, an object of the present invention is to provide an effective method for reducing contamination of in vitro cultures of mature shoot material and shoot material of outdoor origin.

A further object of this invention is to provide an effective method for reducing the frequency of contaminations in in vitro cultures of shoot material from woody and non-woody plants, both juvenile and mature, for the purposes of in vitro rejuvenation, micropropagation, embryogenesis, organogenesis, bud culture, meristem culture, or micrografting for virus elimination.

SUMMARY OF THE INVENTION

The above objectives are achieved by the present method. This method combines the preculture isolation of shoots (to exclude contaminants) with applications of antimicrobial agents (to kill existing contaminants on the shoots) during the initial development of the shoot explants on donor plants. After excision from the donor plant, the shoot explants are surface-sterilized to kill all exposed contaminants. These surface-sterilized shoot explants are subsequently cultured in vitro until harvesting of the new shoot material is desired.

A preferred method follows the procedure noted above except that, instead of directly culturing the surface-sterilized shoot explants in vitro, the surface-sterilized shoot explants are grafted in vitro onto understocks. These grafted explants are subsequently cultured in vitro. This additional step is employed to separate any remaining viable contaminants on the shoot explants from the nutrient medium (thereby further reducing any possibility of contaminant growth).

To accomplish the present method, bags or similar enclosures are first used to cover and isolate single or multiple branches on donor plants. (As used herein the term "branches" includes the main leader or stem of a woody plant, as well as any other parts of a woody plant which may develop shoot material.) It is preferred to prune or otherwise treat the branches (i.e., by application of growth regulators) prior to their isolation in order to stimulate the production of new shoots. Isolation is maintained during the entire time necessary for the appropriate development of shoot explants. Isolating shoots directly on plants growing out-of-doors eliminates the need for the time consuming and often problematic processes of rooting mature shoots or grafting mature shoots onto seedlings so that they can be moved into and grown in a cleaner greenhouse or growth chamber environment.

After the initial isolation of the donor branches in bags, antimicrobial agents are applied periodically to the isolated branches within these bags (particularly to the developing shoots contained within the enclosures). Because of the nature of most tissue culture sterilization procedures, only the outer tissue of the explant which comes in contact with the sterilization agent is disinfected. Therefore, due to their external anatomy many shoots tend to have areas inaccessible to sterilization treatments at the time of culture. To address this problem, multiple applications of antimicrobial agents may be administered to the enclosed branches within the isolating bags during the development of new shoots to ensure that contaminants in difficult-to-reach locations on the shoots are eliminated.

Following the initial two steps (which ensure relatively contaminant-free shoot material) the isolating bags are withdrawn in order that the shoot explants may be removed from the donor plant. These explants are surface-sterilized, then cultured in vitro until new shoot material develops. Thus, by following the present method the practitioner will produce new in vitro shoot material which is virtually free of surface contaminants.

If desired, the resulting surface-sterilized shoot explants may be grafted in vitro onto surface-sterilized seedling understocks or embryo understocks. These understocks (which are commonly grown in a greenhouse, growth chamber, or laboratory) may be accepted as being virtually contaminant-free due to the increased efficiency of surface-sterilization techniques on such understock material. Thus, the understock provides a physical separation between any potential contaminants, which may still be present on the scion, and the nutrient medium. This technique greatly reduces the possibility that any contaminants remaining on the scion material will grow and destroy the culture. The seedling or embryo understock, however, continues to provide the scion explant with the nutrients from the medium necessary for survival and growth.

After new shoot material grows beyond the limits of the original scion, the new material may be carefully excised and cultured independently. Again, by following the present method the practitioner will produce new in vitro shoot material which is virtually free of surface contaminants.

Therefore, the steps of the method may be summarized as follows:

STEP 1. Branches are isolated and sealed at locations where new shoots will develop (especially at newly pruned sites) on donor plants using bags or other similar enclosures. While the donor plants are being cultivated to produce new plant shoots; the isolation is maintained during the entire time necessary for the development of the new shoot explants.

STEP 2. An appropriate antimicrobial agent or combination of agents (such as a fungicide and/or bactericide) is periodically applied inside the bag to the branch and the new shoots during the new shoots' development.

STEP 3. The enclosures are removed and the sufficiently developed new shoot explants are excised from the donor plant.

STEP 4. The new shoot explants are surface-sterilized.

STEP 5. The surface-sterilized new shoot explants are cultured in vitro until harvesting of the new contamination-free in vitro shoot material is desired.

Or, alternatively:

STEP 5. The surface-sterilized new shoot explants are grafted onto surface-sterilized seedling or embryo understocks.

STEP 6. These grafted new shoot explants are cultured in vitro until harvesting of the new contamination-free in vitro shoot material is desired.

DESCRIPTION OF THE PREFERRED EMBODIMENT

Sturdy branches on the donor plant are selected and treated (either by pruning or by application of a suitable growth regulator) at a location appropriate to stimulate the development of new shoots. If needed, a wire support (extending about 10 cm above the pruned location) is then attached to each branch to provide support to the isolating bag. A weather-resistant bag is then placed over each branch and corresponding wire support in order to isolate the branch. It is preferred to equip each bag with a small incision (commonly about 7.0 cm in length) to allow for the foliar application of anti-microbial agents. This opening is kept sealed using a binder clip or other suitable device except during the application of anti-microbial agents. The bottom opening of each bag is sealed around the branch using non-absorbent cotton or polyester fiber-fill and tied shut with twine or wire tie. (While the need for incisions may be eliminated by introducing the anti-microbial agents via the bottom openings of the enclosures, it is preferred to utilize incisions for ease-of-handling purposes.) Isolation in these bags is maintained during the entire time required for development of the new shoots (usually about 2 to 10 weeks).

Immediately following the treatment to stimulate new shoot development and isolation of each branch, a suitable anti-microbial agent or combination of agents (such as broad-spectrum fungicides and/or bactericides) is applied through the sealable opening in the bag to the treated branch enveloped by each bag (after which the opening is again sealed). Thereafter, anti-microbial agents are periodically reapplied (commonly about every 7 to 14 days) to each treated branch and its accompanying developing new shoots. It is within the ability of a skilled artisan to determine the type of fungicide and/or bactericide to be applied to the enclosed branches (as well as the schedule of applications necessary) in order to kill contaminants on the shoots. Applications of the anti-microbial agents are continued throughout the period necessary for the development of the new shoots.

When the new shoots have developed to a suitable size (a minimum of about 0.5 cms for ease-of-handling purposes), the isolating bags are removed and these new shoots are excised from the donor plant. The shoots are subsequently surface-sterilized. One method of surface-sterilization is to utilize a solution of 70% ethanol followed by submersion in a calcium hypochlorite or sodium hypochlorite solution. However, any effective method of surface-sterilization which does not result in excessive harm to the excised shoots may be utilized.

After surface-sterilization, the excised shoots are cultured in vitro under aseptic conditions until harvesting of the new in vitro shoot material is desired.

An alternative, preferred step would be to graft the surface-sterilized excised shoots onto surface-sterilized, seedling understocks or surface-sterilized, embryo understocks. The shoot explants (or portions thereof) are grafted (using a cleft graft or other appropriate grafting methods) under aseptic conditions onto seedling or embryo understocks of sufficient size to prevent contact between the scion and the nutrient medium. The resulting grafted explant is placed in culture, making sure that contact between the scion and the medium is avoided. The cultured explant is subsequently incubated to allow new growth to occur from the scion. When sufficient growth has occurred to allow excision of the new material, the new shoots are removed and cultured independently. This new shoot material will be virtually free of surface contaminants.

Bags which are suitable for use in the present method will be of sufficient size to enclose and isolate the desired area of the branch while also allowing enough room for new shoots to develop appropriately. The bag may be transparent, translucent, or opaque. The pore size of the bags should be large enough to allow sufficient gas exchange for appropriate shoot development while being small enough to hinder the entry of contaminants. Materials which are suitable for use in comprising the bags include, but are not limited to, the following: paper, plastic, cloth, silk, canvas, nylon, rayon, polyester, cellophane, mylar, and combinations thereof.

The donor plant's environment will also effect the type of bag utilized. For example, if the donor plant is out-of-doors, the bag should be weather-resistant to prevent the necessity of replacing the enclosure part-way through the development of the new shoots.

The present method is effective in controlling common external surface contaminants such as fungi, bacteria, and yeasts. Anti-microbial agents which are suitable for use in the present method are those which will kill the above-noted contaminants without harming the plant. Examples of such agents include, but are not limited to, the following: fungicides, bactericides, antibiotics, ethanol and other alcohols, sodium hypochlorite, calcium hypochlorite, hydrogen peroxide, mercuric chloride, and combinations thereof.

Agents which are suitable for use in the surface-sterilization are those which will kill the above-noted contaminants without causing excessive harm to the explant. Examples of such agents include, but are not limited to, the following: fungicides, bactericides, sodium hypochlorite, calcium hypochlorite, alcohols, hydrogen peroxide, mercuric chloride, various commercial sterilants, radiation, fumigants, and combinations thereof. While radiation or fumigation may be utilized for surface-sterilization, it is preferred for ease-of-handling purposes to utilize liquid, chemical sterilization agents. A skilled artisan can easily ascertain the proper strength or solution levels at which to apply the proper anti-microbial agents and/or surface-sterilization agents to achieve the desired results.

The following examples are provided to further illustrate the present invention and are not to be construed as limiting the invention in any manner.

EXAMPLE 1

The following example evaluated three procedures, both alone and in combination, for reducing contamination in cultures of mature shoots of field-grown *Pinus taeda* L. (see Table I below). These procedures included pre-culture isolation of mature shoots, pre-culture foliar application of fungicide to mature shoots, and in vitro grafting of mature shoots onto greenhouse-grown-seedling understocks. Six-year-old trees were utilized as a source of mature material, and newly-developed shoots stimulated by pruning served as the mature shoot explants. Paper DRG pollination bags (commercially available from DRG Packaging, Toronto, Ontario) were used to isolate mature shoots during development in the field. Explants were cultured on solidified nutrient medium contained in culture tubes. Cultures were evaluated for fungal and bacterial contamination during the eight weeks following culture initiation.

Preparation of Seedling Understock Material

Seeds of *Pinus taeda* L. were surface-sterilized by submersion in a 3% $H_2O_2$ solution for 20 minutes. After the $H_2O_2$ treatment the seeds were stratified in the dark at approximately 6° C. for 30 days.

After stratification the seeds were surface-sterilized in a 3% $H_2O_2$ solution as before. Following this treatment the seeds were planted in flats containing soilless potting medium. The flats were placed in full sun in a greenhouse, and watered with reverse osmosis (RO) water when necessary during germination and subsequent seedling growth. Beginning five weeks after planting, the seedlings were sprayed with fungicide once every ten days. The type of fungicide employed was alternated between CLEARY 336WP (commercially available from W.A. Cleary Chemical Corporation, Somerset, N.J.; and utilized in solution at ½ tbl/gal of RO water) and CAPTAN 50WP (commercially available from ICI Americas Inc., Wilmington, Del.; and utilized in solution at 2 tbl/gal of RO water).

Approximately 8–13 weeks after planting (when the appropriate mature shoot material was ready), seedling epicotyls with at least 3.5 cm of visible stem were excised for each set of mature shoots excised at that time for treatments requiring grafting. When harvesting, the epicotyls were placed in a beaker containing RO water to prevent desiccation. Each shoot was then trimmed to 3.5 cm by removing the shoot base, if necessary, and the shoots were placed in 500 ml wide-mouth Erlenmeyer flasks. The shoots were rinsed five times in RO water, followed by a five minute wash in water containing common liquid dishwashing soap (about 10 drops per flask). After removing the soap residue with RO water, the shoots were washed in a 70% ethanol solution for about 30 seconds. The shoots were then surface-sterilized for five minutes in a 20% commercial bleach (1.05% sodium hypochlorite) solution (containing four drops of TWEEN 20 surfactant per liter), followed by three aseptic rinsings with sterile RO water. Finally, each flask of shoots was covered with a sterile petri dish lid and stored in a laminar flow hood until use.

Preparation of Mature Shoot Material

Six healthy well-branched six-year-old trees, each from a different *Pinus taeda* L. family, were selected to provide mature shoot material. Twenty-four sturdy branches of the previous year's growth were selected from the upper crown of each tree. (Branches chosen were those with multiple shoots from the current year's growth.) Each of these branches (along with its accompanying current year's growth) were collectively referred to as a treatment branch. Three treatment branches on each tree were randomly tagged for each of the eight treatments.

When the seedlings for understock material were about five weeks old, all of the treatment branches selected on the six-year-old field-grown trees were pruned. When pruned, one-half of each existing branch of the current year's growth was removed.

For treatments requiring isolation, a wire support was attached to each treatment branch immediately after pruning with the top of the support approximately 10 cm above the top of the pruned portion. A paper DRG pollination bag was then placed over each support and treated branch. The opening at the bottom of each bag was then stuffed until sealed with POLYFIL (commercially available from Fairfield Processing Corporation, Danbury, Conn.); and the bags were tied shut with a twist-tie wire (commercially available from Bel-Art Products, Pequannock, N.J.).

For treatments requiring both isolation and fungicide application, a 7.5 cm slot was cut in the center of the top edge of the bag to allow a small spray nozzle to enter the bag and spray the shoots. To close and seal this small hole, the top of the bag was folded over (folding away from the clear window side of the bag) and clamped shut with a binder clip (commercially available from Officemate International Corporation, Carteret, N.J.). Isolation in these bags was maintained during the entire time required for development of the new shoots.

For treatments requiring fungicide application, the terminal ends of the treatment branches were sprayed with fungicide after pruning and bagging were completed. Fungicide applications were subsequently applied once every ten days, alternating between solutions of CLEARY 3336WP (½ tbl/gal) and CAPTAN 50WP (2 tbl/gal). Treatment branches were sprayed to cover all of the current year's growth until run-off occurred. Applications continued throughout the entire time required for development of the new shoots.

After the treatment branches had been prepared, the shoot tips of all of the remaining branches on the tree were pruned off, including the main leader, to reduce the inhibitive effects that apical dominance might have on new shoot development.

When the majority of the newly developed mature shoots for each treatment on each tree were between 1 to 4 cm in length (approximately five to eight weeks after pruning), the shoots were removed from the trees by carefully twisting them off at the point of attachment to the pruned branch. Collectively, up to 20 mature shoots were removed from the three treatment branches in each treatment on each tree. The mature shoots from each treatment and each tree were kept separate and placed in labeled 125 ml flasks containing RO water. In the laboratory these shoots were washed and surface-sterilized (as previously described for the seedling material). Following sterilization, each flask was covered with a sterile petri dish lid and stored in a laminar flow hood until use.

Culture Initiation and Maintenance

Following surface-sterilization, mature shoots cultured directly or grafted were handled differently. For shoots in treatments not requiring in vitro grafting, each mature shoot was placed on a sterile petri dish and the basal section of stem damaged by the sterilization process was removed using a #10 scalpel blade. For shoots in the treatments requiring in vitro grafting, each mature shoot was grafted onto a seedling understock as described below.

With the aid of a dissecting microscope, mature shoots were grafted onto seedling understocks using a cleft graft. The grafting took place under aseptic conditions just prior to culturing. Following the surface-sterilization of both seedlings and mature shoots, each 3.5 cm seedling shoot was individually removed from a flask and placed on a sterile petri dish. Using a #10 scalpel blade, a 0.5 cm section of stem was removed from each end of the shoot. At the apical end of the shoot section, a 0.5 cm longitudinal cut was made through the stem. At this time a mature shoot from a separate flask was removed and placed on the same sterile petri dish. (From this point on, care was taken not to touch the basal end of the seedling understock with either the mature shoot or any instrument that came in contact with the mature shoot). Using a #10 scalpel blade, the mature shoot was shortened to 1.0 cm of visible stem and then a longitudinal wedge was cut in the base of the shoot, making one cut on each of the two opposite sides of the stem to create a wedge of approximately 30° to 40°. Holding the seedling understock and the mature scion in separate pairs of forceps, the basal wedge of the mature shoot was inserted into the longitudinal cut at the apical end of the seedling shoot section, thus forming the cleft graft union. In joining the scion with the understock, the surface of the scion was lined up with the outer surface of the understock on at least one side of the graft union to ensure cambial contact. Care was taken to make sure that the scion and understock fit snug together and that no gaps existed in the graft union.

Following preparation of grafted and ungrafted shoots, the resulting explants were carefully placed in 25×150 mm culture tubes, with the basal 0.5 cm of each explant inserted into a gel-solidified nutrient medium (dispensed in 20 ml portions). The culture tubes were closed using MAGENTA 2-way caps (commercially available from Magenta Corporation, Chicago, Ill.) and sealed with NESCOFILM (commercially available from Karlan Research Products Corporation, Santa Rosa, Calif.) to prevent exterior contaminants from entering.

The cultures were incubated in a culture room for eight weeks at 25° C., under a 16 hour photoperiod of approximately 60 $\mu E \cdot s^{-1} \cdot m^{-2}$ light (VITALITE fluorescent bulbs commercially available from Duro-test Corporation, Fairfield, N.J.). At one week intervals, beginning seven days after initiation of each treatment, the presence or absence, and type of contamination was recorded for each culture by visual observation. The different treatments are noted in Table I below, while the results of the treatments are listed in Table II.

TABLE I

Eight treatments examining the effects of the presence or absence of three procedures on reducing contamination in cultures of mature loblolly pine shoots.

| Treatment # | Isolation | Fungicide | Grafted |
| --- | --- | --- | --- |
| 1* | 0 | 0 | 0 |
| 2 | + | 0 | 0 |
| 3 | 0 | + | 0 |
| 4 | 0 | 0 | + |
| 5 | + | + | 0 |
| 6 | + | 0 | + |
| 7 | 0 | + | + |
| 8 | + | + | + |

*Treatment 1 is the control.
0 = procedure not applied, while + = procedure applied.

TABLE II

Results from evaluation of Isolation (I), Fungicide application (F), and in vitro Grafting (G) for controlling in vitro contamination.

| Treatment | Treatment Description | # of cultures | % of contaminated cultures |
| --- | --- | --- | --- |
| 1 | Control | 120 | 97 |
| 2 | I | 106 | 92 |
| 3 | F | 120 | 81 |
| 4 | G | 120 | 94 |
| 5 | I + F | 74 | 53 |
| 6 | I + G | 103 | 91 |
| 7 | F + G | 120 | 67 |
| 8 | I + F + G | 85 | 52 |

Results

Individual procedures (treatments 2–4) resulted in a small reduction (3–16%) in overall contamination (Table II above). These individual procedures, when utilized alone or when combined with another procedure, had a profound effect on the proportion of contaminations involving specific contaminants. Both isolation and fungicide application significantly reduced fungal contaminations, while in vitro grafting was effective in reducing bacterial contaminations.

Combinations of procedures (treatments 5–8) significantly reduced overall culture contaminations compared with cultures of untreated control shoots (Table II). The combination including both isolation and fungicide resulted in a reduction in overall contamination from 97% seen in the untreated control shoots, down to 53%. The combination of all three procedures resulted in greatest reduction in overall contamination, down to 52% compared with 97% seen in the untreated control shoots.

EXAMPLE 2

The following example evaluated two combinations of procedures for reducing contamination in cultures of mature shoots of field-grown Pinus taeda L. (see Table III below). These procedures included pre-culture isolation of mature shoots, pre-culture foliar application of fungicide to mature shoots, and in vitro grafting of mature shoots onto greenhouse-grown seedling understocks. Nine- and ten-year-old trees were utilized as a source of mature material, and newly-developed shoots stimulated by pruning served as the mature shoot explants. Non-woven polyester DURAWELD pollination bags (commercially available from PBS International, Scarborough, North Yorkshire, United Kingdom) were used to isolate mature shoots during development in the field. Explants were cultured on solidified nutrient medium contained in culture tubes. Cultures were evaluated for fungal and bacterial contamination during the eight weeks following culture initiation.

Preparation of Seedling Understock Material

Seeds of Pinus taeda L. were surface-sterilized by submerging in a 3% $H_2O_2$ solution for 20 minutes. After the $H_2O_2$ treatment, the seeds were stratified in the dark at approximately 6° C. for 30 days.

After stratification, the seeds were surface-sterilized in 3% $H_2O_2$ as before. Following this treatment the seeds were planted in flats containing soilless potting medium. The flats were placed in full sun in a greenhouse, and watered with reverse osmosis (RO) water when necessary during germination and subsequent seedling growth. Beginning five weeks after planting, the seedlings were sprayed with fungicide once every ten days, alternating between solutions of CLEARY 3336WP (½ tbl/gal) and CAPTAN 50WP (2 tbl/gal).

Approximately 8–13 weeks after planting (when the appropriate mature shoot material was ready), seedling epicotyls with at least 3.5 cm of visible stem were excised for each set of mature shoots excised at that time for the treatment requiring grafting. When harvesting, the epicotyls were placed in a beaker containing RO water to prevent desiccation. Each shoot was then trimmed to 3.5 cm by removing the shoot base (where necessary) prior to being placed in 500 ml wide-mouth Erlenmeyer flasks. The shoots were rinsed five times in RO water, followed by a five minute wash in a aqueous solution of liquid dishwashing soap (10 drops per flask). After removing the soap residue with RO water, the shoots were washed in 70 percent ethanol for 30 seconds. Following this, the shoots were surface-sterilized for five minutes in a 20% solution of commercial bleach (1.05% sodium hypochlorite) containing four drops TWEEN 20 surfactant per liter, and then aseptically rinsed three times with sterile RO water. Each flask of shoots was then covered with a sterile petri dish lid and stored in a laminar flow hood until use.

Preparation of Mature Shoot Material

Several healthy, well-branched trees, representing four genotypes which were nine to ten years of age were selected to provide mature shoot material. As many as eight sturdy branches of the previous year's growth were selected from the middle to upper crown of each tree to serve as treatment branches.

When the seedlings for understock material were five weeks old, all of the treatment branches selected on the mature, field-grown trees were pruned. Each treatment branch was pruned back to the previous year's growth.

For treatments requiring isolation, a wire support was attached to each treatment branch immediately after pruning, with the top of the support approximately 10 cm above the top of the pruned portion. A non-woven polyester DURAWELD pollination bag was then placed over each support and treated branch. The opening at the bottom of each bag was then stuffed using POLYFIL, and the bags were tied shut with a twist-tie wire. For treatments requiring both isolation and fungicide application, a 7.5 cm slot was cut in the center of the top edge of the bag to allow a small spray nozzle to enter the bag and spray the shoots. To close and seal this small hole, the top of the bag was folded over (folding away from the clear window side of the bag) and clamped shut with a binder clip. Isolation in these bags was maintained during the entire time required for development of the new shoots.

For treatments requiring fungicide application, the terminal ends of the treatment branches were sprayed with fungicide after pruning and bagging were completed. Fungicide applications were then subsequently made once every two weeks, alternating between solutions of CLEARY 3336WP (½ tbl/gal) and CAPTAN 50WP (2 tbl/gal). Treatment branches were sprayed to cover the pruned site and all newly developed shoots until run-off occurred. Applications continued throughout the entire time required for development of the new shoots.

When the majority of the newly developed mature shoots for each treatment on each tree were between 1 to 4 cm in length (approximately five to eight weeks after pruning), they were removed from the trees by carefully twisting them off at the point of attachment to the pruned branch. The mature shoots from each treatment and each genotype were kept separate and placed in labeled 125 ml flasks containing RO water. In the laboratory, these shoots were washed and surface-sterilized via the procedure described above for the seedling material. Following sterilization, each flask was covered with a sterile petri dish lid and stored in a laminar flow hood until use.

Culture Initiation and Maintenance

Following surface-sterilization, mature shoots cultured directly or grafted were handled differently. For shoots in treatments not requiring in vitro grafting, each mature shoot was placed on a sterile petri dish and the basal section of stem damaged by the sterilization process was removed using a #10 scalpel blade. For shoots in the treatments requiring in vitro grafting, each mature shoot was grafted onto a seedling understock as described below.

With the aid of a dissecting microscope, mature shoots were grafted onto seedling understocks using a cleft graft. The grafting took place under aseptic conditions just prior to culturing. Following the surface-sterilization of both seedlings and mature shoots, each 3.5 cm seedling shoot was individually removed from a flask and placed on a sterile petri dish. Using a #10 scalpel blade, a 0.5 cm section of stem was removed from each end of the shoot. At the apical end of the shoot section, a 0.5 cm longitudinal cut was made through the stem. At this time a mature shoot from a separate flask was removed and placed on the same sterile petri dish. (From this point on, care was taken not to touch the basal end of the seedling understock with either the mature shoot or any instrument that came in contact with the mature shoot). Using a #10 scalpel blade, the mature shoot was shortened to 1.0 cm of visible stem and then a longitudinal wedge was cut in the base of the shoot, making one cut on each of the two opposite sides of the stem to create a wedge of approximately 30° to 40°. Holding the seedling understock and the mature scion in separate pairs of forceps, the basal wedge of the mature shoot was inserted into the longitudinal cut at the apical end of the seedling shoot section, thus forming the cleft graft union. In joining the scion with the understock, the surface of the scion was lined up with the outer surface of the understock on at least one side of the graft union to ensure cambial contact. Care was taken to make sure that the scion and understock fit snug together and that no gaps existed in the graft union.

Following preparation of grafted and ungrafted shoots, the resulting explants were carefully placed in 25×150 mm culture tubes, with the basal 0.5 cm of each explant inserted into a gel-solidified nutrient medium (dispensed in 20 ml portions). The culture tubes were closed using MAGENTA 2-way caps and sealed with NESCOFILM to prevent exterior contaminants from entering.

The cultures were incubated in a culture room for eight weeks at 25° C., under a 16 hr photoperiod of approximately 60 $\mu E \cdot s^{-1} \cdot m^{-2}$ light (VITA-LITE fluorescent bulbs). At one week intervals, beginning seven days after initiation of each treatment, the presence or absence, and type of contamination was recorded for each culture by visual observation. The different treatments are noted in Table III below, while the results of the treatments are listed in Table IV.

TABLE III

Three treatments examining the effectiveness of combining various procedures on reducing contamination in cultures of mature loblolly pine shoots.

| Treatment # | Isolation | Fungicide | Grafted |
|---|---|---|---|
| 1* | 0 | 0 | 0 |
| 2 | + | + | 0 |
| 3 | + | + | + |

*Treatment 1 is the control.
0 = procedure not applied, while + = procedure applied.

TABLE IV

Results from the evaluation of various combinations of isolation (I), fungicide application (F), and in vitro grafting (G) for controlling in vitro contamination.

| Treatment | Treatment Description | # of cultures | # of contaminated cultures |
|---|---|---|---|
| 1 | Control | 30 | 100 |
| 2 | I + F | 28 | 93 |
| 3 | I + F + G | 30 | 33 |

Results

In this example, the combination of shoot isolation and fungicide application reduced the incidence of culture contamination from 100% seen in the untreated control shoots down to 93% (see TABLE IV). However, the combination of all three procedures, isolation, fungicide application, and in vitro grafting, resulted in a reduction in contamination from 100% seen with the untreated control shoots, down to 33% (Table 4).

Summary

The procedures of isolation, fungicide application, and in vitro grafting, when utilized alone, provided marked reduction in contamination with cultures of mature shoots of loblolly pine. Generally, combinations of two of these procedures provided a more substantial reduction in overall contamination. However, the greatest and most significant reduction in culture contamination was consistently achieved by combining all three procedures.

Many modifications and variations of the present invention will be apparent to one of ordinary skill in the art in light of the above teachings. It is therefore understood that the scope of the invention is not to be limited by the foregoing description, but rather is to be defined by the claims appended hereto.

BIBLIOGRAPHY

Aitken-Christie, J., and M. Connett. Micropropagation of forest trees. In Transplant Production Systems. K. Kurata and T. Kozai (eds). *Kluwer Academic Publishers*, The Netherlands, 1992.

Berthon, J.-Y., N. Boyer, and T. Gaspar. Uptake, distribution and metabolism of 2,4-dichlorophenoxyacetic acid in shoots of juvenile and mature clones of *Sequoiadendron giganteum* in relation to rooting in vitro. *Plant Physiology and Biochemistry* 29:355–362, 1991.

da Câmara Machado, M. L., A. da Câmara Machado, V. Hanzer, B. Kalthoff, H. Weiβ, D. Mattanovich, F. Regner, and H. Katinger. 1991. A new, efficient method using 8-hydroxy-quinolinol-sulfate for the initiation and establishment of tissue cultures of apple from adult material. *Plant Cell, Tissue and Organ Culture* 27:155–160, 1991.

Duhem, K., N. Le Mercier, and Ph. Boxus. Difficulties in the establishment of axenic in vitro cultures of field collected coffee and cacao germplasm. *Acta Horticulturae* 225:67–75, 1988.

Debergh, P. C., and L. J. Maene. A scheme for commercial propagation of ornamental plants by tissue culture. *Scientia Horticulturae* 14:335–345, 1981.

Enjalric, F., M. P. Carron, and L. Lardet. Contamination of primary cultures in tropical areas: The case of *Hevea Brasiliensis*. *Acta Horticulturae* 225: 57–65, 1988.

Hammerschlag, F. A., G. R. Bauchan, and R. Scorza. Factors influencing in vitro multiplication and rooting of peach cultivars. *Plant Cell, Tissue and Organ Culture* 8:235–242, 1987.

Jones, O. P., and W. C. C. Hadlow. Juvenile-like character of apple trees produced by grafting scions and rootstocks produced by micropropagation. *Journal of Horticultural Science* 64:395–401, 1989.

Jones, O. P., C. A. Pontikis, and M. E. Hopgood. Propagation in vitro of five apple scion cultivars. *Journal of Horticulture Science* 54:155–158, 1979.

Leifert, C., and W. M. Waites. Contaminants of plant tissue cultures. *International Association of Plant Tissue Culture Newsletter* 60:2–13, 1990.

Marks, T. R. Micropropagation of hardy ornamental nursery stock. In Micropagation in Horticulture: Practice and Commercial Problems. P. G. Alderson and W. M. Dullforce, (eds), 1986. Proceedings of the Institute of Horticulture Symposium, University of Nottingham School of Agriculture, Mar. 24–26, 1986.

Monteuuis, O. In vitro meristem culture of juvenile and mature *Sequoiadendron giganteum*. *Tree Physiology* 3:265–272, 1987.

Oliphant, J. L. Consideration of juvenility and maturity in the micropropagation of the *Metrosideros* species. *Acta Horticulturae* 227:482–484, 1988.

Pliego-Alfaro, F., and T. Murashige. Possible rejuvenation of adult avocado by graftage onto juvenile rootstocks in vitro. *HortScience* 22:1321–1324, 1987.

Polito, V. S., and V. Alliata. Growth of calluses derived from shoot apical meristems of adult and juvenile English ivy (*Hedera helix* L.). *Plant Science Letters* 22:387–393, 1981.

Poulsen, G. B. Elimination of contaminating microorganisms from meristem culture of apple rootstock M26. *Acta Horticulturae* 225:193–197, 1988.

Preece, J. E., C. A. Huetteman, W. C. Ashby, and P. L. Roth. Micro- and cutting propagation of silver maple. I. Results with adult and juvenile propagules. *Journal of the American Society of Horticultural Science* 116:142–148, 1991.

Robbins W. J., and A. Hervey. Tissue culture of callus from seedling and adult stages of *Hedera helix*. *American Journal of Botany* 57:452–457, 1970.

Sanchez, M. C., and A. M. Vieitez. In vitro morphogenic competence of basal sprouts and crown branches of mature chestnut. *Tree Physiology* 8:59–70, 1991.

Struve, D. K., and R. D. Lineberger. Restoration of high adventitious root regeneration potential in mature *Betula papyrifera* Marsh. softwood stem cuttings. *Canadian Journal of Forest Research* 18:265–269, 1988.

Sudarsono and R. G. Goldy. Growth regulator and axillary bud position effects on in vitro establishment of *Vitis rotundifolia*. *HortScience* 26:304–307, 1991.

Warrag, E. I, M. S. Lesney, and D. L. Rockwood. Micropropagation of field tested superior *Eucalyptus grandis* hybrids. *New Forests* 4:67–79, 1990.

What is claimed is:

1. A method for reducing contamination of in vitro cultures of shoot material from woody plants which comprises:

(a) placing a bag over a branch of a donor plant at locations where new plant shoots will develop and sealing the bag in order to isolate that portion of the branch which is enveloped in the bag from contaminants;

(b) cultivating the donor plant to produce new plant shoots on the isolated portion of the branch;

(c) periodically applying an antimicrobial agent to the branch inside the bag at appropriate time intervals so as to reduce microbial contaminants on the branch during the time the branch is isolated in the bag and resealing the bag after each application so as to maintain the isolation of the branch;

(d) after a period of time sufficient for development of new plant shoots, removing the bag and excising new plant shoot explants from that portion of the branch which had been isolated;

(e) surface-sterilizing the explants;

(f) grafting the surface-sterilized explants onto surface-sterilized understocks; and (g) culturing the grafted explants in vitro to develop new contamination-free in vitro shoot material.

2. The method of claim 1 wherein the branch is the main leader of the donor plant.

3. The method of claim 1 wherein the development of new plant shoots is stimulated by pruning the donor plant's branch prior to isolation of the branch.

4. The method of claim 1 wherein the development of new plant shoots is stimulated by applying growth regulators to the donor plant's branch prior to isolation of the branch.

5. The method of claim 1 wherein the bag is made of material selected from the group consisting of paper, plastic, and combinations thereof.

6. The method of claim 5 wherein the plastic is selected from the group consisting of cellophane, polyester, nylon, and combinations thereof.

7. The method of claim 1 wherein the antimicrobial agent is selected from the group consisting of fungicides, bactericides, antibiotics, alcohols, sodium hypochlorite, calcium hypochlorite, hydrogen peroxide, mercuric chloride, and combinations thereof.

8. The method of claim 1 wherein surface-sterilization is performed via application of a member selected from the group consisting of fungicides, bactericides, sodium hypochlorite, calcium hypochlorite, alcohols, hydrogen peroxide, mercuric chloride, radiation, fumigants, and combinations thereof.

9. The method of claim 1 wherein the new plant shoots have developed to a size of at least 0.5 centimeters prior to the bag being removed and the new plant shoots being excised.

10. The method of claim 1 wherein the understocks are selected from the group consisting of seedling understocks and embryo understocks.

* * * * *

UNITED STATES PATENT AND TRADEMARK OFFICE
CERTIFICATE OF CORRECTION

PATENT NO. : 5,712,164
DATED : January 27, 1998
INVENTOR(S) : Jay E. Coke

It is certified that error appears in the above-identified patent and that said Letters Patent is hereby corrected as shown below:

On the title page, first column, under OTHER PUBLICATIONS, da Câmara Machado reference, delete "Weiss" and substitute therefor --Weiß--.

On the title page, first column, under OTHER PUBLICATIONS, Hammerschlag reference, delete "R.R. Bauchan" and substitute therefor --G.R. Bauchan--.

In column 6, line 58, delete "336WP" and substitute therefor --3336WP--.

Signed and Sealed this

Twenty-second Day of December, 1998

Attest:

BRUCE LEHMAN

*Attesting Officer*          *Commissioner of Patents and Trademarks*